United States Patent
Zadno-Azizi et al.

(10) Patent No.: US 6,312,407 B1
(45) Date of Patent: Nov. 6, 2001

(54) OCCLUSION OF A VESSEL

(75) Inventors: Gholam-Reza Zadno-Azizi, Newark; Celso J. Bagaoisan, Union City; Mukund R. Patel; Ketan P. Muni, both of San Jose, all of CA (US)

(73) Assignee: Medtronic PercuSurge, Inc., Sunnyvale, CA (US)

( * ) Notice: Subject to any disclaimer, the term of this patent is extended or adjusted under 35 U.S.C. 154(b) by 0 days.

(21) Appl. No.: 09/026,106

(22) Filed: Feb. 19, 1998

Related U.S. Application Data

(63) Continuation-in-part of application No. 08/650,464, filed on May 20, 1996, now abandoned, which is a continuation-in-part of application No. 08/464,579, filed on Jun. 6, 1995, now Pat. No. 5,833,650.

(51) Int. Cl.[7] .......................... A61M 29/00; A61M 25/00; A61M 5/00; A61M 31/00
(52) U.S. Cl. .................... 604/103.03; 604/104; 604/109; 604/99.01; 604/509; 604/264; 604/528; 606/198
(58) Field of Search ..................................... 604/507–509, 604/96, 99, 104–109, 528, 96.01, 99.01, 103.03, 523, 538; 606/191, 194, 198

(56) References Cited

U.S. PATENT DOCUMENTS

| | | |
|---|---|---|
| 3,620,212 | 11/1971 | Fannon, Jr. et al. . |
| 3,834,394 | 9/1974 | Hunter et al. . |

(List continued on next page.)

FOREIGN PATENT DOCUMENTS

| | | |
|---|---|---|
| 0 321 912 A1 | 12/1988 | (EP) . |
| 0 737 450 A1 | 10/1996 | (EP) . |
| 0 784 991 A2 | 7/1997 | (EP) . |
| 0 791 340 A1 | 8/1997 | (EP) . |
| 0 820 784 A2 | 1/1998 | (EP) . |
| 2 020 557 | 11/1979 | (GB) . |

(List continued on next page.)

OTHER PUBLICATIONS

A Vena Cava Filter Using Thermal Shape Memory Alloy, Morris Simon, M.D., Roy Kaplow, Ph.D., Edwin Salzman, M.D., and David Frieman, M.D., *Diagnostic Radiology*, vol. 125, pp. 89–94, Oct. 1977.

Shape–Memory Alloys, L. McDonald Schetky, *Scientific American*, vol. 241, No. 5, pp. 74–82, Nov. 1979.

(List continued on next page.)

*Primary Examiner*—William E. Kamm
*Assistant Examiner*—Patricia M Bianco
(74) *Attorney, Agent, or Firm*—Knobbe, Martens, Olson & Bear, LLP

(57) ABSTRACT

A device for occluding a vessel employs one of a number of different expansion members joined to one or more elongate members. The expansion member may include a braid, one or more coils, ribs, a ribbon-like structure, a slotted tube, or a filter-like mesh. If the expansion member is enclosed by a suitable membrane, the device seals with the vessel wall to partially or completely occlude the vessel. A perforated membrane may be used to permit the perfusion of blood. The expansion member may be self-expanding, or it may be expanded by engaging it with one of the elongate members. Alternatively, the expansion member may be expanded by heating it.

33 Claims, 10 Drawing Sheets

U.S. PATENT DOCUMENTS

| | | |
|---|---|---|
| 3,890,977 | 6/1975 | Wilson . |
| 4,233,690 | 11/1980 | Akins . |
| 4,411,655 | 10/1983 | Schreck . |
| 4,425,908 | 1/1984 | Simon . |
| 4,427,000 | 1/1984 | Ueda . |
| 4,445,892 | 5/1984 | Hussein et al. . |
| 4,456,011 | 6/1984 | Warnecke . |
| 4,494,531 | 1/1985 | Gianturco . |
| 4,573,966 | 3/1986 | Weikl et al. . |
| 4,619,246 | 10/1986 | Molgaard-Nielsen et al. . |
| 4,650,466 | 3/1987 | Luther . |
| 4,723,549 | 2/1988 | Wholey et al. . |
| 4,771,777 | 9/1988 | Horzewski et al. . |
| 4,794,928 | 1/1989 | Kletschka . |
| 4,832,028 | 5/1989 | Patel . |
| 4,832,055 | 5/1989 | Palestrant . |
| 4,873,978 | 10/1989 | Ginsburg . |
| 4,921,478 | 5/1990 | Solano et al. . |
| 4,921,484 | 5/1990 | Hillstead . |
| 4,926,858 | 5/1990 | Gifford, III et al. . |
| 5,000,743 | 3/1991 | Patel . |
| 5,025,799 | 6/1991 | Wilson . |
| 5,053,008 | 10/1991 | Bjaj . |
| 5,064,434 | 11/1991 | Haber . |
| 5,102,415 | 4/1992 | Guenther et al. . |
| 5,108,419 | 4/1992 | Reger et al. . |
| 5,135,484 | 8/1992 | Wright . |
| 5,167,239 | 12/1992 | Cohen et al. . |
| 5,178,618 | 1/1993 | Kandarpa . |
| 5,188,602 | 2/1993 | Nichols . |
| 5,250,060 | 10/1993 | Carbo et al. . |
| 5,256,146 | 10/1993 | Ensminger et al. . |
| 5,263,964 | 11/1993 | Purdy . |
| 5,267,960 | 12/1993 | Hayman et al. . |
| 5,281,200 | 1/1994 | Corso, Jr. et al. . |
| 5,282,824 | 2/1994 | Gianturco . |
| 5,318,576 | 6/1994 | Plassche, Jr. et al. . |
| 5,328,471 | 7/1994 | Slepian . |
| 5,329,942 | 7/1994 | Gunther et al. . |
| 5,342,306 | 8/1994 | Don Michael . |
| 5,380,284 | 1/1995 | Don Michael . |
| 5,419,774 | 5/1995 | Willard et al. . |
| 5,456,667 * | 10/1995 | Ham et al. ............................ 604/107 |
| 5,458,574 | 10/1995 | Machold et al. . |
| 5,465,717 | 11/1995 | Imran et al. . |
| 5,484,384 | 1/1996 | Fearnot . |
| 5,484,412 | 1/1996 | Pierpont . |
| 5,490,859 | 2/1996 | Mische et al. . |
| 5,497,782 | 3/1996 | Fugoso . |
| 5,501,694 | 3/1996 | Ressemann et al. . |
| 5,507,768 | 4/1996 | Lau et al. . |
| 5,507,771 | 4/1996 | Gianturco . |
| 5,527,338 | 6/1996 | Purdy . |
| 5,540,658 | 7/1996 | Evans et al. . |
| 5,540,707 | 7/1996 | Ressemann et al. . |
| 5,549,626 | 8/1996 | Miller . |
| 5,573,508 | 11/1996 | Thornton . |
| 5,607,445 | 3/1997 | Summers . |
| 5,607,466 | 3/1997 | Imbert et al. . |
| 5,643,171 | 7/1997 | Bradshaw et al. . |
| 5,658,309 | 8/1997 | Berthiaume et al. . |
| 5,662,671 | 9/1997 | Barbut et al. . |
| 5,674,198 | 10/1997 | Leone . |
| 5,683,411 | 11/1997 | Kavteladze et al. . |
| 5,693,067 | 12/1997 | Purdy . |
| 5,695,519 | 12/1997 | Summers et al. . |
| 5,720,764 | 2/1998 | Naderlinger . |
| 5,766,203 | 6/1998 | Imran et al. . |
| 5,769,816 | 6/1998 | Barbut et al. . |
| 5,769,871 | 6/1998 | Mers Kelly et al. . |
| 5,795,322 | 8/1998 | Boudewijn . |
| 5,810,874 | 9/1998 | Lefebvre . |
| 5,814,064 | 9/1998 | Daniel et al. . |
| 5,827,324 | 10/1998 | Cassell et al. . |
| 5,836,968 | 11/1998 | Simon et al. . |
| 5,846,260 | 12/1998 | Maahs . |
| 5,895,410 | 4/1999 | Forber et al. . |
| 5,895,411 | 4/1999 | Irie . |
| 5,910,154 | 6/1999 | Tsugita et al. . |
| 5,911,734 | 6/1999 | Tsugita et al. . |
| 5,935,139 | 8/1999 | Bates . |
| 5,968,064 | 10/1999 | Selmon et al. . |
| 6,001,118 | 12/1999 | Daniel et al. . |
| 6,059,814 | 5/2000 | Ladd . |

FOREIGN PATENT DOCUMENTS

| | | |
|---|---|---|
| WO 83/01894 | 6/1983 | (WO) . |
| WO 92/21282 | 12/1992 | (WO) . |
| WO 96/01591 | 1/1996 | (WO) . |
| WO 93/12723 | 8/1996 | (WO) . |
| WO 96/22736 | 8/1996 | (WO) . |
| WO 96/31174 | 10/1996 | (WO) . |
| WO 96/39998 | 12/1996 | (WO) . |
| WO 97/17100 | 5/1997 | (WO) . |
| WO 97/31672 | 9/1997 | (WO) . |
| WO 98/33443 | 8/1998 | (WO) . |
| WO 98/46297 | 10/1998 | (WO) . |
| WO 98/50103 | 11/1998 | (WO) . |
| WO 99/02093 | 1/1999 | (WO) . |
| WO 99/16362 | 4/1999 | (WO) . |
| WO 99/22673 | 5/1999 | (WO) . |
| WO 99/23976 | 5/1999 | (WO) . |
| WO 99/44542 | 9/1999 | (WO) . |
| WO 00/16705 | 3/2000 | (WO) . |

OTHER PUBLICATIONS

Alloys With Two–Way Shape Memory Effect, K.N. Melton, O. Mercier, *Mechanical Engineering*, p. 42–43, Mar. 1980.

Percutaneous Removal of Small Gallstones—In Vivo Comparison of Baskets, G.D. Rubin, G.R. Wittich, R.M. Walter, D.C. Swanson, *Journal of Interventional Radiology*, pp. 29–31, 1992.

* cited by examiner

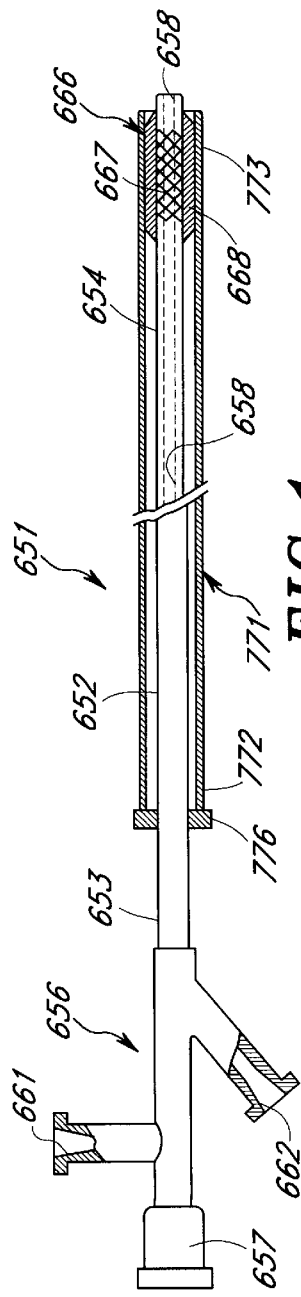
FIG.1
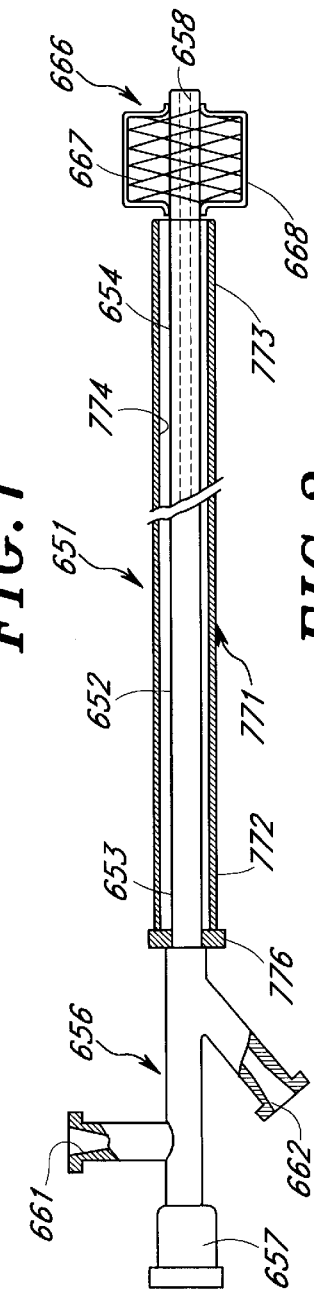
FIG.2
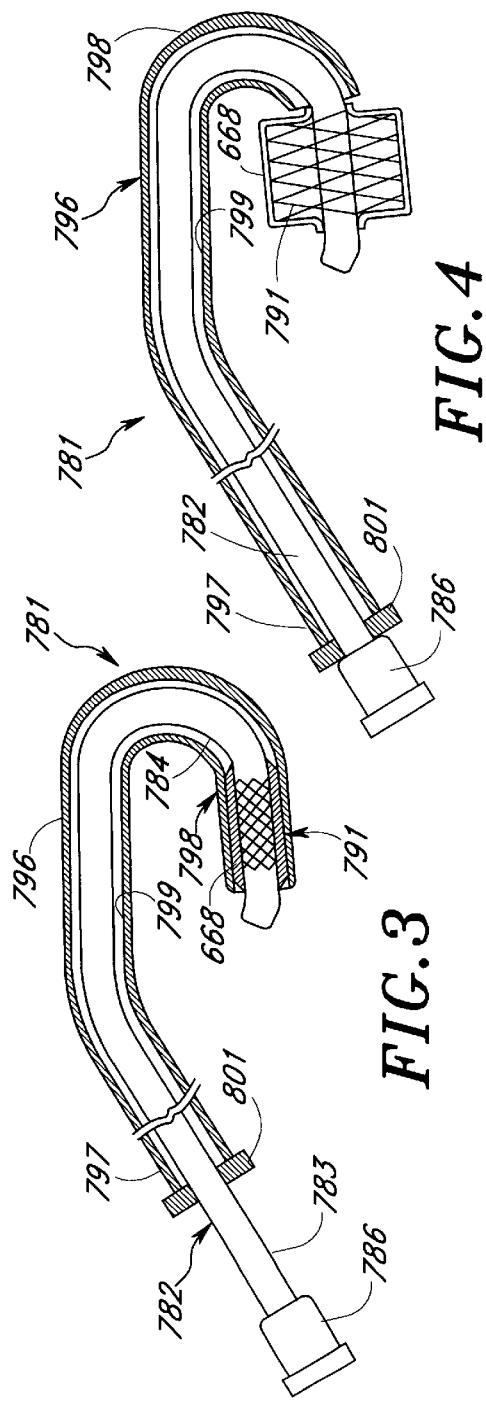
FIG.3
FIG.4

OCCLUSION OF A VESSEL

RELATED APPLICATIONS

This application is a continuation in part of an earlier filed application (Ser. No. 08/650,464 filed May 20, 1996); now abandoned, which is in turn a continuation in part of an application (Ser. No. 08/464,579) filed Jun. 6, 1995, now U.S. Pat. No. 5,833,650.

Details regarding the centering of intravascular devices used in radiation treatment are described in Assignee's co-pending U.S. application Ser. No. 09/026,103 filed Feb. 19, 1998, entitled Intravascular Radiation Therapy Device, and Method of Use, which is hereby incorporated by reference.

BACKGROUND OF THE INVENTION

1. Field of the Invention

The present invention relates generally to the occlusion of a vessel within a patient, and more specifically, to an apparatus and method of partially or completely occluding a vessel.

2. Description of the Related Art

Attempts heretofore have been made to treat occlusions in the carotid arteries leading to the brain. However, such arteries have been very difficult to treat because of the possibility of dislodging plaque which can enter various arterial vessels of the brain and cause permanent brain damage. Attempts to treat such occlusions with balloon angioplasty have been very limited because of such dangers. In surgical treatments, such as endarterectomy, the carotid artery is slit and plaque is removed from the vessel in the slit area. Such surgical procedures have substantial risk associated with them which can lead to morbidity and mortality.

In other procedures, such as in angioplasty and in the treatment of peripheral arteries and veins, there is the possibility that the guide wires and catheters used in such procedures during deployment of the same may cause dislodgement of debris or emboli which can flow downstream and cause serious damage, such as stroke, if they occlude blood flow in smaller vessels. Thus, in summary, embolization and migration of micro-emboli downstream to an end organ is a major concern of cardiologists during catheterizations.

There is therefore need for new and improved apparatus and methods which make it possible to treat occluded vessels without endangering the patient.

SUMMARY OF THE INVENTION

The present invention satisfies the need for a device that occludes a vessel, in particular, a vessel in a patient undergoing therapeutic or other medical treatment. Any one of a number of different expansion members are joined to one or more elongate members such as hypotubes to form a device that completely or partially occludes a vessel within a patient. The expansion member may be self-expanding, it may be expanded by engaging it with one of the elongate members, or it may be heated to cause it to expand. A membrane preferably surrounds the expansion member so that a seal is made between the membrane and the vessel. The perfusion of blood is allowed if the membrane is perforated. Partial occlusion may be obtained without a membrane if a suitable expansion member is chosen. In general, in one aspect of the present invention, there is provided an apparatus and method that can be used with approved diagnostic and therapeutic devices to reduce the chance of emboli migrating downstream. Alternatively, the expansion member may anchor an intravascular device within a vessel.

One embodiment of the present invention is a device for occluding a vascular segment, in which the device includes an expansion member and first and second elongate members. The first elongate member engages the expansion member, and the second elongate member surrounds the first elongate member, with the expansion member expanding to occlude the vascular segment when one of the elongate members is moved longitudinally. The expansion member preferably includes a braid, a coil, a ribbon-like structure, a slotted tube, a plurality of ribs or a filter-like mesh. The device may also include material that adjoins the expansion member for creating a partial or total seal with the vascular segment.

In one particular embodiment, the expansion member is in an unexpanded state when it is surrounded by the second elongate member, but expands when the first elongate member is pushed through the second elongate member. In another embodiment, both the first and second elongate members are secured to the expansion member, and the expansion member expands as the first elongate member is retracted.

Another embodiment of the invention is a method of occluding a segment within a vessel, which includes the step of inserting first and second elongate members into the vessel to be occluded (in which the first elongate member adjoins an expansion member), followed by the step of varying the position of at least one of the elongate members so that the expansion member expands until the vessel is completely or partially occluded. In one embodiment, the varying step includes retracting one of the elongate members, and in another embodiment, the varying step comprises pushing one of the elongate members through the other elongate member.

In yet another method of occluding a segment within a vessel, an expansion member is inserted within the vessel, and the expansion member is heated to cause it to expand until the vessel is at least partially occluded. Heating the expansion member may involve, for example, passing electrical current through it or passing warm solution over or near it.

BRIEF DESCRIPTION OF THE DRAWINGS

FIG. 1 is a side-elevational view in section of one embodiment of a catheter apparatus incorporating the present invention for treating occluded vessels.

FIG. 2 is a side-elevational view in section similar to FIG. 1 but showing the apparatus in FIG. 1 with the expansion member (in this case, a self-expandable seal) deployed.

FIG. 3 is a side-elevational view in section of another embodiment of a catheter apparatus incorporating the present invention for treating occluded vessels.

FIG. 4 is a view similar to FIG. 3 but showing the expansion member (in this case, a self-expandable seal) deployed.

DETAILED DESCRIPTION OF THE PREFERRED EMBODIMENTS

Figure 5:
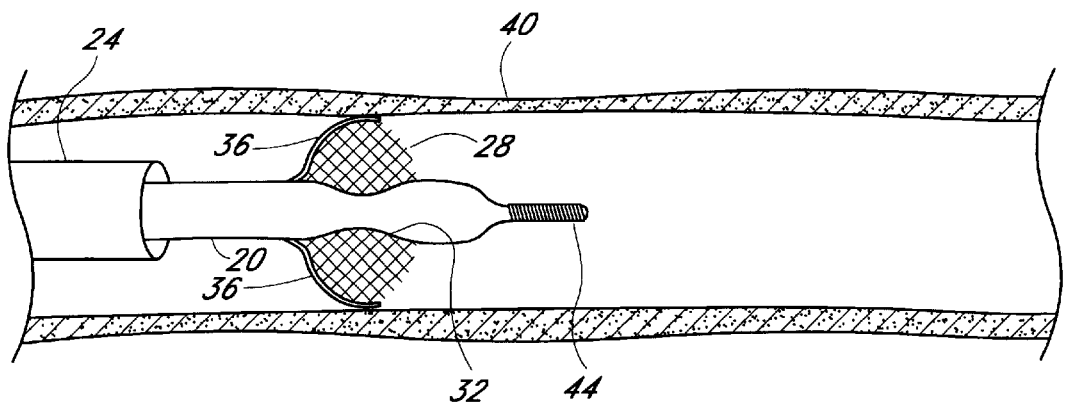
FIG. 5 is a schematic, longitudinal cross sectional view of an embodiment in which a membrane only partially surrounds a braid used as the expansion member.

The expansion members discussed herein include braids, coils, ribs, ribbon-like structures, slotted tubes, and filter-like meshes. These expansion members may be partially covered or completely surrounded by a membrane or other covering to provide occlusion or sealing of the vessel. As used herein, "occlusion" or "sealing", and the like, mean partial or complete blockage of fluid flow in a vascular segment, as it is sometimes preferable to allow perfusion. Moreover, such expansion members may be deployed by various mechanical means, electrical means or thermomechanical means, etc., as described herein. Expansion members that are deployed mechanically are preferably "spring-like" in nature, i.e. they are preferably resilient to facilitate their deployment or retraction.

Catheter Apparatuses and Self-Expanding Braids

One embodiment of a catheter apparatus incorporating the present invention for treating occluded vessels is shown in FIGS. 1 and 2. As shown therein, the catheter apparatus 651 consists of a flexible elongate member 652 which is provided with proximal and distal extremities 653 and 654. A conventional adapter 656 is mounted on the proximal extremity and is provided with a Touhy-Borst fitting 657 which is in communication with a large central lumen 658 extending from the proximal extremity 653 to the distal extremity 654. An aspiration fitting 661 is provided on the adapter 656 as well as an irrigation fitting 662, both of which are in communication with the central lumen 658. However, it should be appreciated that if desired, separate lumens can be provided in the flexible elongate member 652 for both of the fittings 661 and 662.

Self-expanding sealing mechanism 666 is mounted on the distal extremity 654. This self-expanding sealing mechanism 666 can take any suitable form. For example, as shown it can consist of a braided structure 667 formed of a suitable shape memory material such as a nickel titanium alloy that will attempt to expand to a predetermined shape memory. Other than shape memory materials, other materials such as stainless steel, Elgiloy™, titanium or other materials can be utilized in the braid 667 as long as they have the capability of expanding when the self-expanding seal mechanism is released. Also it should be appreciated that the self-expanding seal mechanism 666 can be comprised of an absorbent material which when it absorbs saline or blood expands to form a seal. Such seals can be readily accomplished because it is only necessary to form a seal of approximately 1.5 psi to prevent small particles from moving downstream.

In order to prevent abrasion of a vessel, it is desirable to cover the braided structure 667 with a covering 668 of a suitable material such as a polymer or a biocompatible coating which extends over the braided structure 667 and which moves with the braided structure 667 as it expands and contracts. The polymer can be of a suitable material such as silicone, C-flex, polyethylene or PET which would form a good sealing engagement with the wall of the artery. The covering 668 may be perforated to allow perfusion.

A mechanism is provided for compressing the self-expanding sealing mechanism 666 so that the apparatus can be inserted into a vessel and consists of an elongate sleeve 771 having proximal and distal extremities 772 and 773 and a bore 774 extending from the proximal extremity 772 to the distal extremity 773. A collar 776 is mounted on the proximal extremity 772 of the sleeve 771 and is positioned near the adapter 656. The collar 776 serves as a mechanism for retracting the sleeve as shown in FIG. 2 to uncover the self-expanding sealing mechanism 666 after the catheter has been deployed to permit the self-expanding sealing mechanism 666 to expand and form a seal with the arterial vessel adjacent the stenosis to be treated.

Another embodiment of a catheter apparatus for treating occluded vessels incorporating the present invention is shown in FIGS. 3 and 4. As shown therein, the apparatus 781 consists of a guiding catheter 782 having proximal and distal extremities 783 and 784. As shown, the distal extremity 784 is provided with a pre-formed bend of a conventional type. A conventional attachment 786 is mounted on the proximal extremity 783. Self-expanding seal mechanism 791 is mounted on the distal extremity 784 and is of the type hereinbefore described in connection with the embodiments shown in FIGS. 1 and 2. A sleeve 796 similar to the sleeve 771 of the previous embodiment is provided in the present embodiment for encasing the self-expanding seal mechanism 791 and for releasing the same after it has been disposed in an appropriate position within a vessel adjacent the occlusion to be treated. Thus, a sleeve 796 is provided having proximal and distal extremities 797 and 798 and having a bore 799 extending from the proximal extremity to the distal extremity which is sized so that it can receive the guide catheter 782. It is provided with a collar 801 on its proximal extremity which is adapted to be disposed outside the patient and which is adapted to be grasped by the physician for pulling the sleeve 796 proximally to uncover the self-expanding seal 791 after the apparatus has been deployed to permit the self-expansion of the sealing mechanism 791 to form a seal with the vessel wall as shown in FIG. 4.

In accordance with the hereinbefore described descriptions, it is apparent that the apparatus can be readily deployed and serve the same function as the main catheter. To accomplish this, the assembly 781 can be introduced into the femoral artery and the distal extremity advanced into the desired location in the arterial vessel. After it has been properly positioned, the physician can retract the sleeve 796 to permit the self-expanding seal mechanism 791 to expand and to form a seal with the wall of the arterial vessel to occlude the arterial vessel and interrupt the flow of blood in the vessel to provide a working space distal of the occlusion formed. This prevents small particles which may thereafter be dislodged from moving downstream. Since a central lumen is available, the therapeutic procedures hereinbefore described can be employed with the catheter apparatus shown in FIGS. 1, 2, 3 and 4.

Although the self-expanding sealing mechanism 666 (791) can be deployed by retracting the sleeve 771 (796) as previously described, the sealing mechanism can also be deployed by pushing the flexible elongate member 652 (guiding catheter 782) through the sleeve so that the sealing mechanism can expand. This may be the preferred way of deploying the sealing mechanism 666 (791), if there is little clearance between the apparatus 651 (781) and the vessel within which the apparatus resides, to reduce the risk of damaging the patient's vessel. As discussed below in connection with subsequent figures, the sealing mechanism 666 (791) may alternatively comprise members such as a coil, a ribbon-like structure, a slotted tube, or a filter-like mesh. In each case, the sealing mechanism expands to partially or completely occlude the vessel in question, or alternatively, to anchor an intravascular device to the vessel.

Alternative Self-Expanding Members

Another embodiment using a braided structure is shown schematically in FIG. 5, in which a flexible elongate member 20 is disposed within a second elongate member 24 such as a hypotube. A self expanding mechanism 28 such as a braided structure is secured to the distal end of the elongate member 20, preferably within an indentation 32 of member 20. The braided structure 28 is only partially encapsulated by a preferably elastomeric membrane 36 that makes a seal with the patient's vessel 40. (Alternatively, a coating such as a polymeric coating may be used in place of the membranes disclosed herein.) In this and the other embodiments, adhesive may be used to secure the self-expanding mechanism 28 and the membrane 36 to the elongate member 20. In the embodiment of FIG. 5, the braided structure 28 and membrane 36 are designed to be asymmetrical, with more material being concentrated at the proximal side of the structure 28. The braids of the embodiments disclosed herein may be stainless steel 304 or 400, superelastic or heat activated Nitinol, an iron base shape memory alloy, or a polymer base, such as polyethylene or polypropylene. They may be constructed, for example, by using standard equipment such as a braider.

Although the embodiment of FIG. 5 shows the flexible elongate member 20 connected to a guidewire tip 44, other technologies for guiding the device through the patient's vessel 40 may be used in this and the other embodiments, such as a guidewire (either over the wire or single operator) or the exchange catheter method, as is well known in the art. Also, although not explicitly shown in the embodiment of FIG. 5 and the other embodiments herein, these embodiments may include lumens, aspiration and irrigation fittings, and collars like those illustrated in FIGS. 1–4.

Figure 6A:
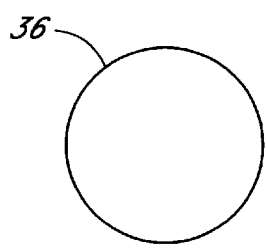
FIGS. 6A and 6B show end views of unperforated and perforated membranes, respectively.
Figure 6B:
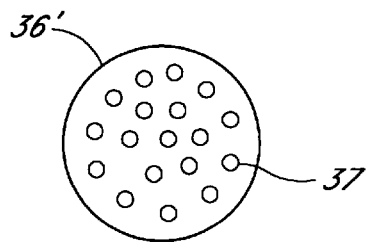

The membrane 36 is preferably impervious to the flow of blood (FIG. 6a) for those applications not requiring perfusion, although a perforated membrane 36' (FIG. 6b) having numerous holes 37 therein may be used in other applications to allow the passage of blood. The holes 37 are preferably greater than 10 microns in diameter and may be up to 80 microns or more in diameter to permit the passage of blood cells (nominally 6–10 microns in diameter) through the membrane 36' while blocking larger particulates such as emboli. Likewise, a perforated membrane 36' may be used in the other embodiments disclosed herein. Antithrombogenic coatings can be used (e.g., heparin) to prevent thrombosis formation.

Figure 7:
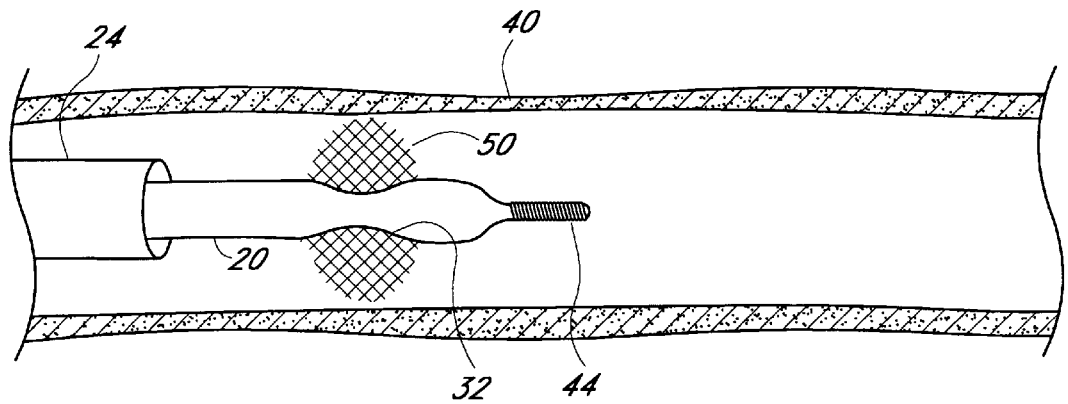
FIG. 7 is a schematic, longitudinal cross sectional view of an embodiment in which a braid without a membrane is used.

FIG. 7 shows an embodiment in which a braided structure 50 is not enclosed by a membrane. When the braided structure 50 comprises, for example, a diamond mesh pattern in which adjacent wires are separated by about 10–80 microns, the braided structure permits the passage of red blood cells, while blocking the flow of matter that may be undesirable, e.g., emboli or other particulates that may be formed or dislodged during medical procedures. Thus, this embodiment is well suited for applications for which perfusion is required.

Figure 8:
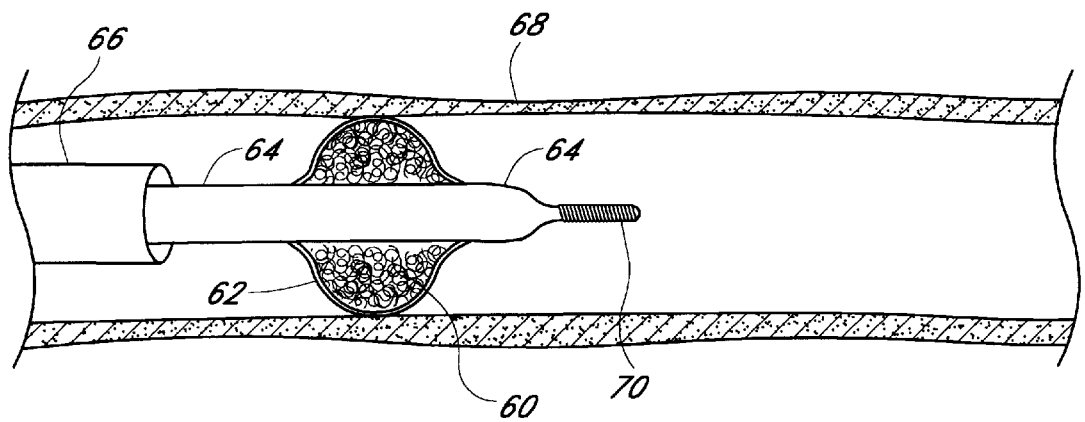
FIG. 8 is a schematic, longitudinal cross sectional view of an embodiment in which a filter-like mesh is used as the expansion member.
Figure 9:
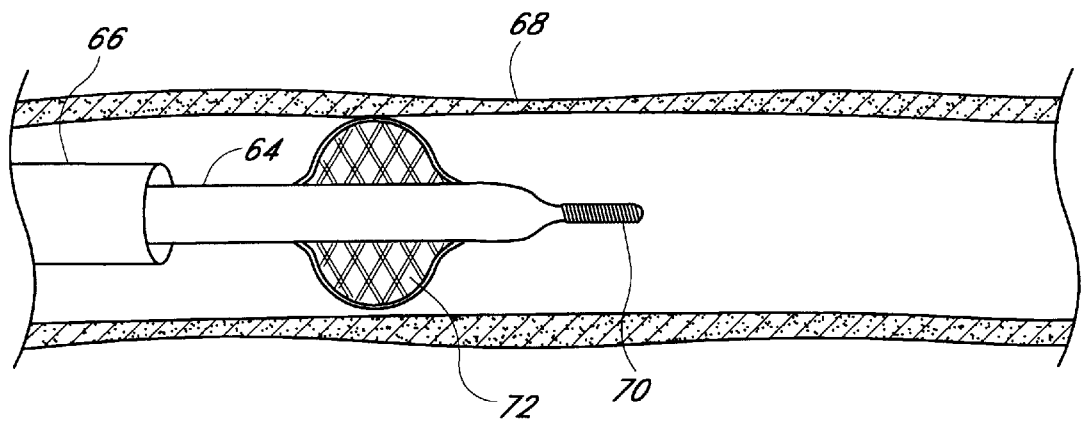
FIG. 9 is a schematic, longitudinal cross sectional view of an embodiment in which a slotted tube is used as the expansion member.
Figure 10:
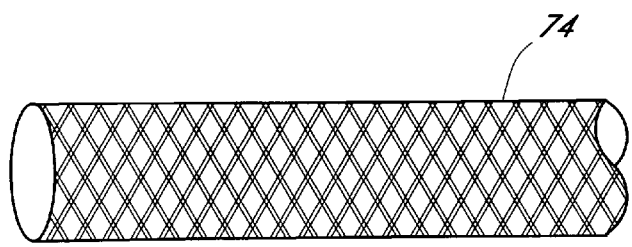
FIG. 10 is a perspective view of the slotted tube used in the embodiment of FIG. 9.

Alternative self-expanding media are shown in FIGS. 8 and 9. In FIGS. 8 and 9, a self-expanding filter-like mesh 60 and a self-expanding slotted tube 72, respectively, are surrounded by a membrane 62 that is preferably elastomeric. The filter-like mesh 60 (or slotted tube 72) and membrane 62 are bonded or otherwise secured to a flexible elongate member 64, e.g., to an indentation therein. As with the other self-expanding media disclosed herein, the filter-like mesh 60 (or slotted tube 72) expands from its unexpanded state when the flexible elongate member 64 is pushed through a second elongate member 66, or alternatively, when the second elongate member 66 is retracted over the first elongate member 64. The filter-like mesh 60 (or slotted tube 72) then expands so that the membrane 62 forms a seal with the surrounding vessel 68. A guidewire tip 70 aids in guiding the device through the vessel 68. The filter-like mesh 60 and slotted tube 72 are of a suitable shape memory material such as Nitinol or (304 or 400) stainless steel. The filter-like mesh 60 is fibrous in nature, being somewhat analogous to steel wool. The slotted tube 72 has a lattice-like appearance. The slotted tube 72 may be constructed, for example, by irradiating a thin-walled tube with a laser beam to form holes in the tube in the shape of polygons such as oblong quadrilaterals. An unexpanded, slotted tube 74 is shown in FIG. 10.

Figure 11:
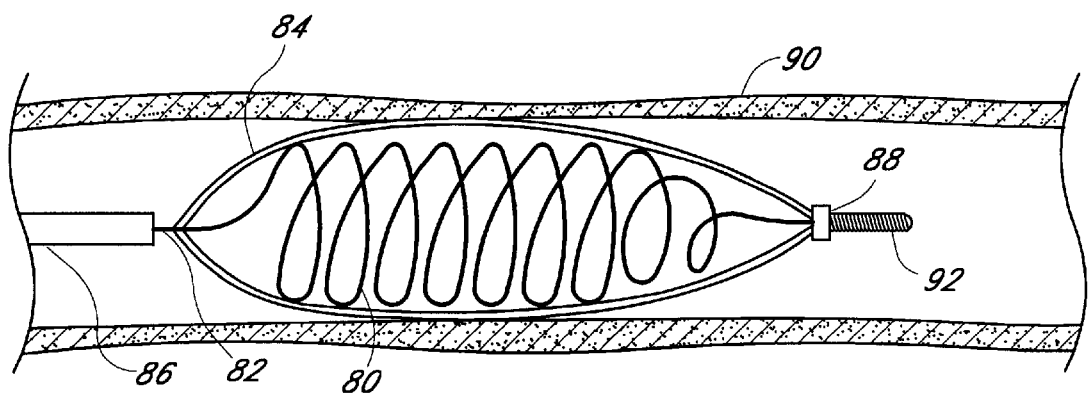
FIG. 11 is a schematic, longitudinal cross sectional view of an embodiment in which a coil is used as the expansion member, and the proximal end of a membrane surrounding the coil adjoins the coil.

FIG. 11 illustrates another embodiment, in which a coil 80 serves as the self-expanding mechanism. The coil 80 may be integrally formed with a first elongate member 82 or be otherwise specially joined to it, e.g., by welding or brazing the coil to the elongate member 82. The coil 80 is surrounded by a membrane 84 that expands with the coil when it is pushed out of a second elongate member 86, or alternatively, when the second elongate member 86 is retracted from the coil 80. Thus, the membrane forms a seal with the surrounding vessel 90. The membrane 84 may be attached directly to the first elongate member 82, or to a member 88 such as a disk that is in turn secured to the coil 80 or the first elongate member 82. A guidewire tip 92 for guiding the device through the vessel 90 may be attached to the first elongate member 82 or to the member 88, if one is used.

Figure 12:
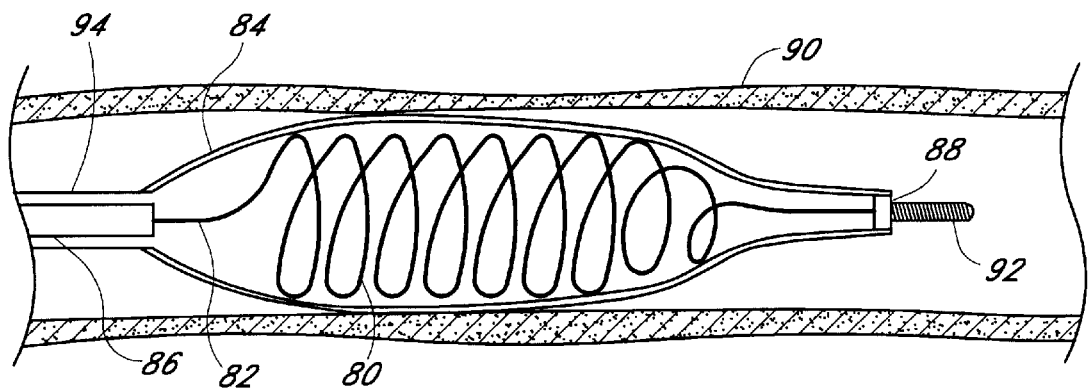
FIG. 12 is a schematic, longitudinal cross sectional view of an embodiment in which a coil is used as the expansion member, and the proximal end of a membrane surrounding the coil adjoins a sheath that surrounds both first and second elongate members.

An embodiment similar to that shown in FIG. 11 is illustrated in FIG. 12, in which the membrane 84 is secured at the proximal end to a separate sheath 94. In this case, the sheath 94 and the first elongate member 82 are extended together over and through, respectively, the second elongate member 86. Assembly may require preloading the coil 80 through the distal end of the second elongate member 86.

Figure 13:
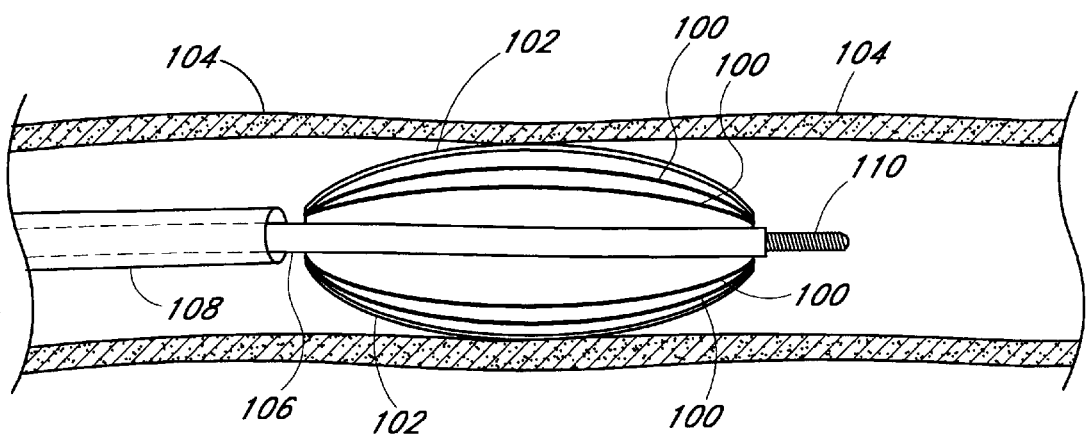
FIG. 13 is a schematic, side cross sectional view of an embodiment in which a plurality of ribbons are used as the expansion member.

Another embodiment that employs a self-expanding medium is shown in FIG. 13, in which a plurality of ribbons 100 make contact with a membrane 102 while they expand to urge the membrane towards the wall of the vessel 104 where it makes a seal. The ribbons 100 of this embodiment are preferably secured to a first elongate member 106 at both ends of the ribbons, by, for example, gluing them in place. The ribbons may be 0.001–0.004"×0.005–0.020"×0.25–1.0" strips of Nitinol, stainless steel, or Elgiloy™ which expand when urged out of the second elongate member 108. A guidewire tip 110 may be used for guiding the device through the vessel and is preferably secured to the distal end of the first elongate member 106.

Figure 14:
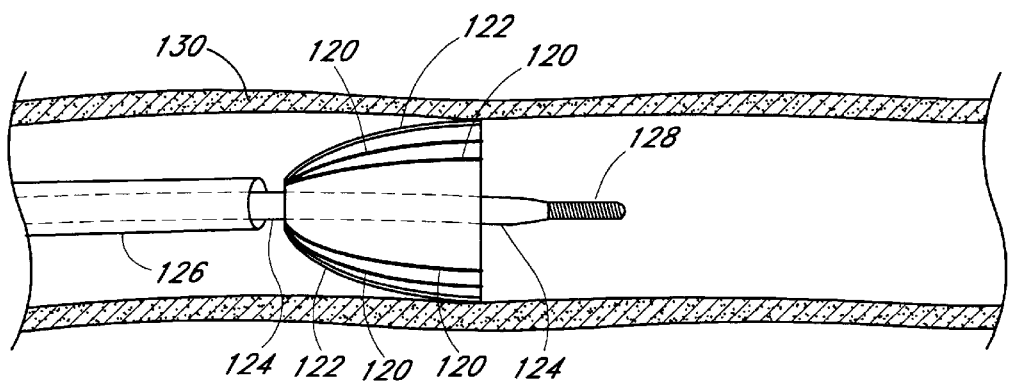
FIG. 14 is a schematic, side cross sectional view of an embodiment in which a plurality of ribs are used as the expansion member.

FIG. 14 illustrates an embodiment similar to the one in FIG. 13, in which ribs 120 such as wires form a series of semicircular arcs when they expand. The ribs 120 are surrounded by a membrane 122 that expands with the ribs to form a seal with the vessel 124. The number of ribs 120 is preferably at least three. The ribs 120 are preferably attached directly to a first elongate member 124 that is surrounded by a second elongate member 126. The ribs 120 themselves are preferably made of a shape memory material such as Nitinol or stainless steel. A guidewire tip 128 aids in guiding the device through the vessel 130.

As in the other self-expanding embodiments, the self-expanding mechanism 100 (120) is in an unexpanded state when enclosed by the second elongate member 108 (126), and expands when pushed or pulled beyond the second elongate member 108 (126).

Non-self-expanding embodiments
1. Heat activated embodiments

Figure 12A:
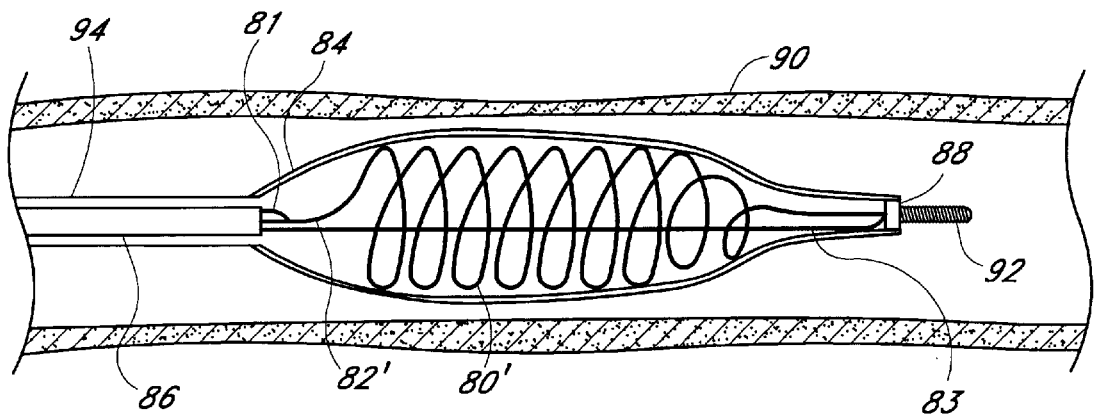
FIG. 12A is an embodiment similar to that shown in FIG. 12, in which resistive heating is used to expand the expansion member, with current being conducted through wires being attached to either side of the expansion member. The expansion member as shown is partially deployed.
Figure 12B:
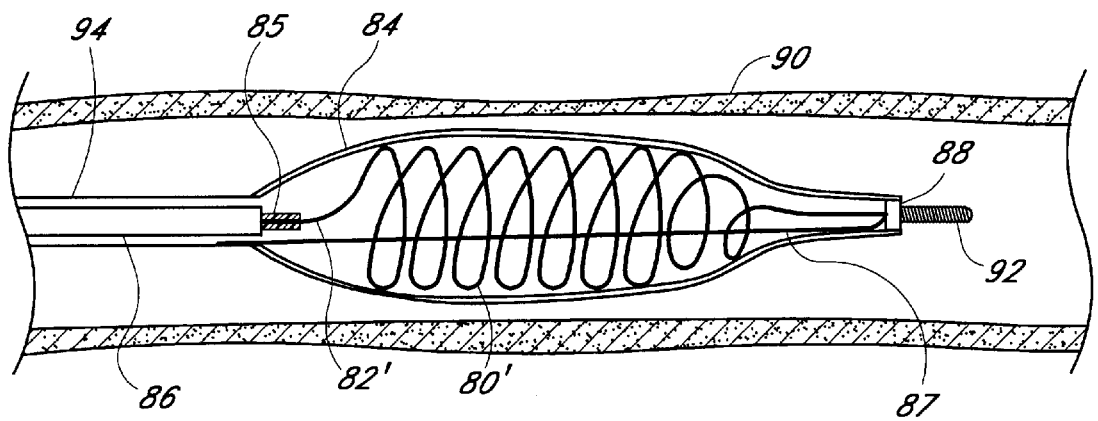
FIG. 12B is an embodiment similar to that shown in FIG. 12A, in which resistive heating is used to expand the expansion member, with current being conducted through a wire being attached to the distal end of the expansion member and through a coating on the first elongate member. The expansion member as shown is partially deployed.

FIGS. 12A and 12B illustrate how electrical means can be used to generate heat to expand an expansion member. A first elongate member 82' (and a coil 80' which adjoins it, coil 80' and member 82' being similar to their unprimed counterparts) is preferably made of heat activated Nitinol, an iron base shape memory alloy, or another material that expands when exposed to heat. As shown in FIG. 12A, low profile, low resistivity electrical lines 81 and 83 preferably pass either through or along the second elongate member 86 and are attached (e.g., soldered) to the first elongate member 82' on either side of the coil 80'. When current is applied through the electrical lines 81 and 83 (the power supply is not shown but is preferably outside the patient), the coil 80' heats up through resistive heating, and the coil expands to urge the membrane 84 to contact the vessel wall 90. Alternatively, as shown in FIG. 12B, the first elongate member 82' may have a coating 85 of gold or silver. In this embodiment, the coated elongate member 82' is used to pass current (with most of the current preferably being carried by the coating 85, so that most of the energy is deposited in the coil 80'), with the circuit being completed with a low resistivity wire 87 that is preferably connected (e.g., soldered) to either the second elongate member 86 or the sheath 94. This principle of resistive heating to expand a expansion member can be applied to the other embodiments disclosed herein as well.

Figure 13A:
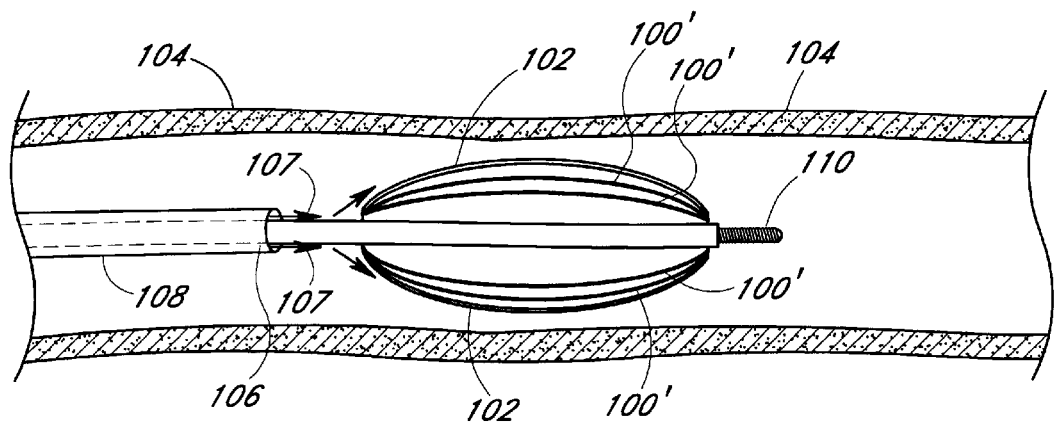
FIG. 13A is an embodiment similar to that shown in FIG. 13, in which a warm solution passes between the first and second elongate members to transfer heat to the expansion member, causing it to expand. The expansion member as shown is partially deployed.
Figure 13B:
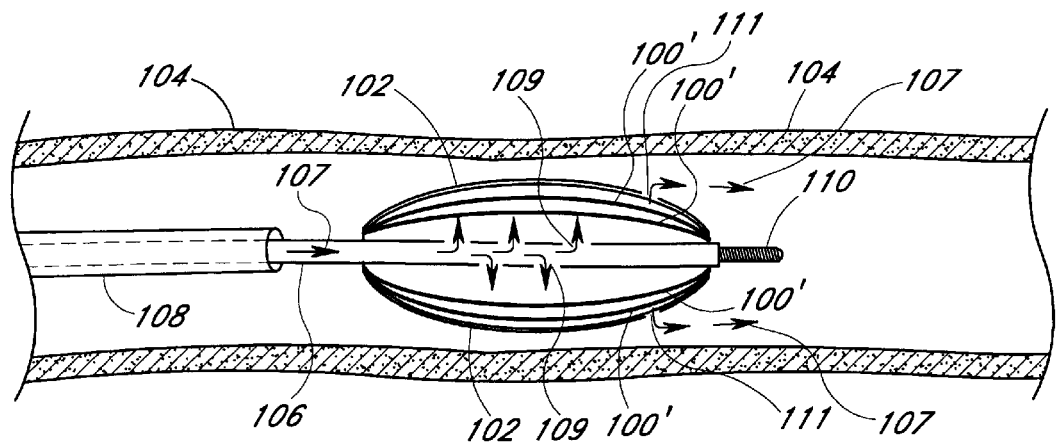
FIG. 13B is an embodiment similar to that shown in FIG. 13A, in which a warm solution passes through the first elongate member to transfer heat to the expansion member, causing it to expand. The expansion member as shown is partially deployed.
Figure 13C:
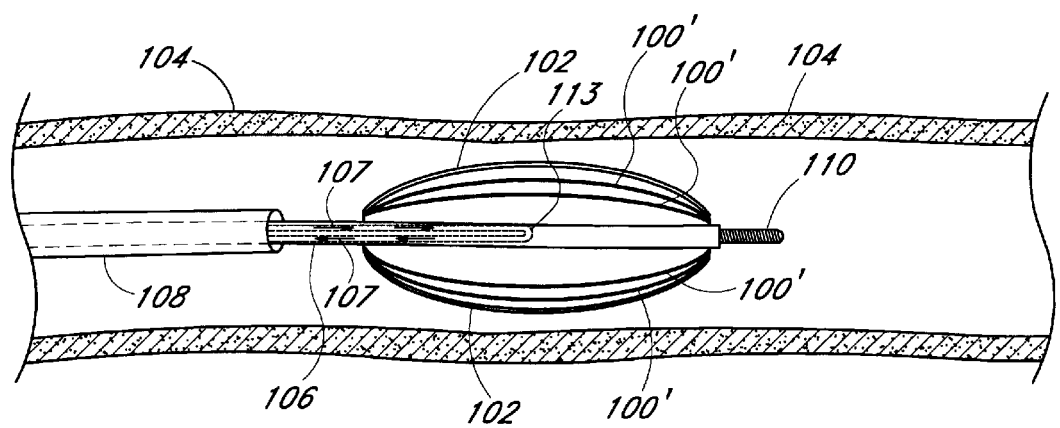
FIG. 13C is an embodiment similar to that shown in FIGS. 13A and 13B, in which a warm solution passes through one or more lumens in the first elongate member to transfer heat to the expansion member, causing it to expand. The expansion member as shown is partially deployed.

FIGS. 13A, 13B, and 13C illustrate how heat transfer using a liquid can deploy an expansion member. The ribbons 100' are preferably made of heat activated Nitinol, an iron base shape memory alloy, or another material that expands when exposed to heat. In the embodiment of FIG. 13A, a warm saline solution 107 is passed between the first and second elongate members 106 and 108 and then over the membrane 102, so that heat is transferred to the ribbons 100'. As the ribbons 100' heat up, they expand, thereby urging the membrane 102 against the vessel wall 104. As illustrated in FIG. 13B, the warm saline solution 107 may also be passed through the first elongate member 106 and then through holes 109 in member 106 so that the saline solution 107 more directly transfers heat to the ribbons 100'. In this embodiment, one or more holes 111 in the membrane 102 (distal to where the seal with the vessel wall 104 is made) may be used to allow the saline solution 107 to flow away beyond the ribbons 100' after heat transfer to the ribbons occurs. As illustrated in FIG. 13C, the saline solution 107 may also be passed through one or more closed loop coils or lumens 113 within the first elongate member 106. In this way, the ribbons 100' and the patient's blood are not exposed directly to any solution. Using heat transfer can also be applied to the other embodiments disclosed herein, provided the expansion member is suitably constructed.

2. Mechanically deployed embodiments

Figure 15:
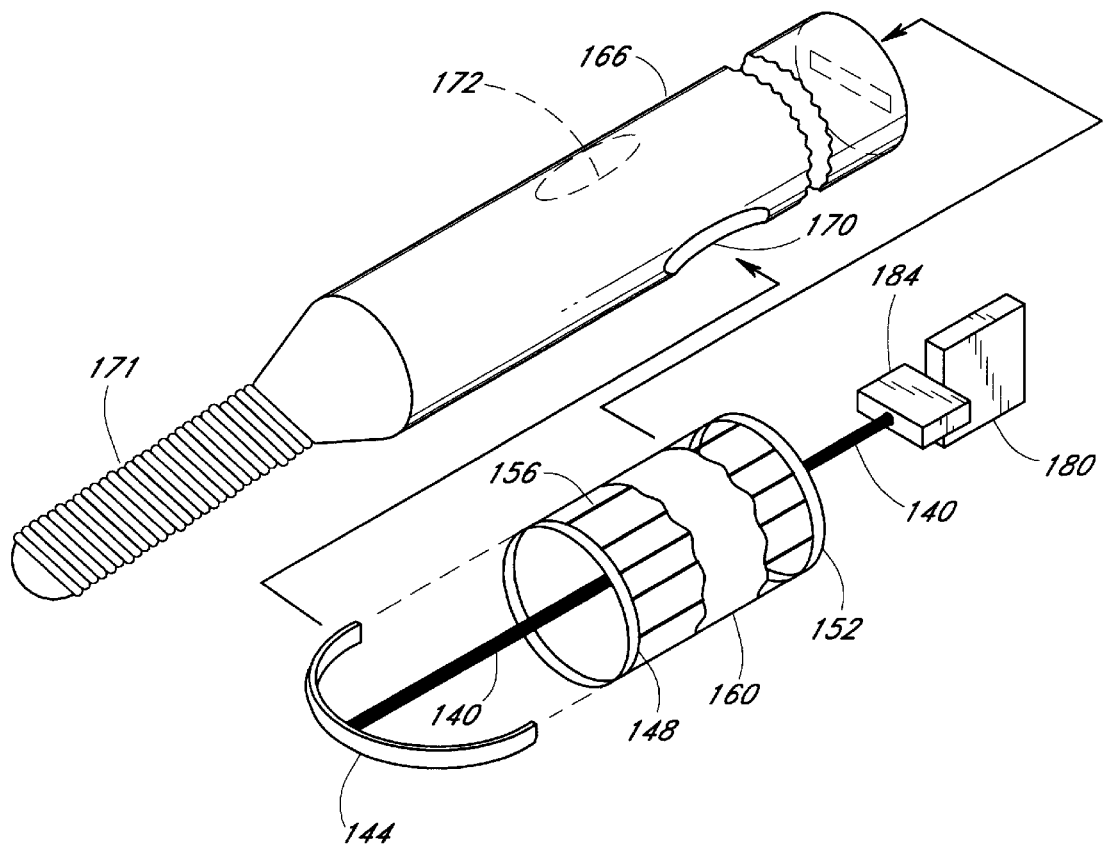
FIG. 15 is an isometric view of an embodiment of the invention in which a pull wire is used to deploy a plurality of non-self-expanding ribbons surrounded by a membrane.
Figure 16:
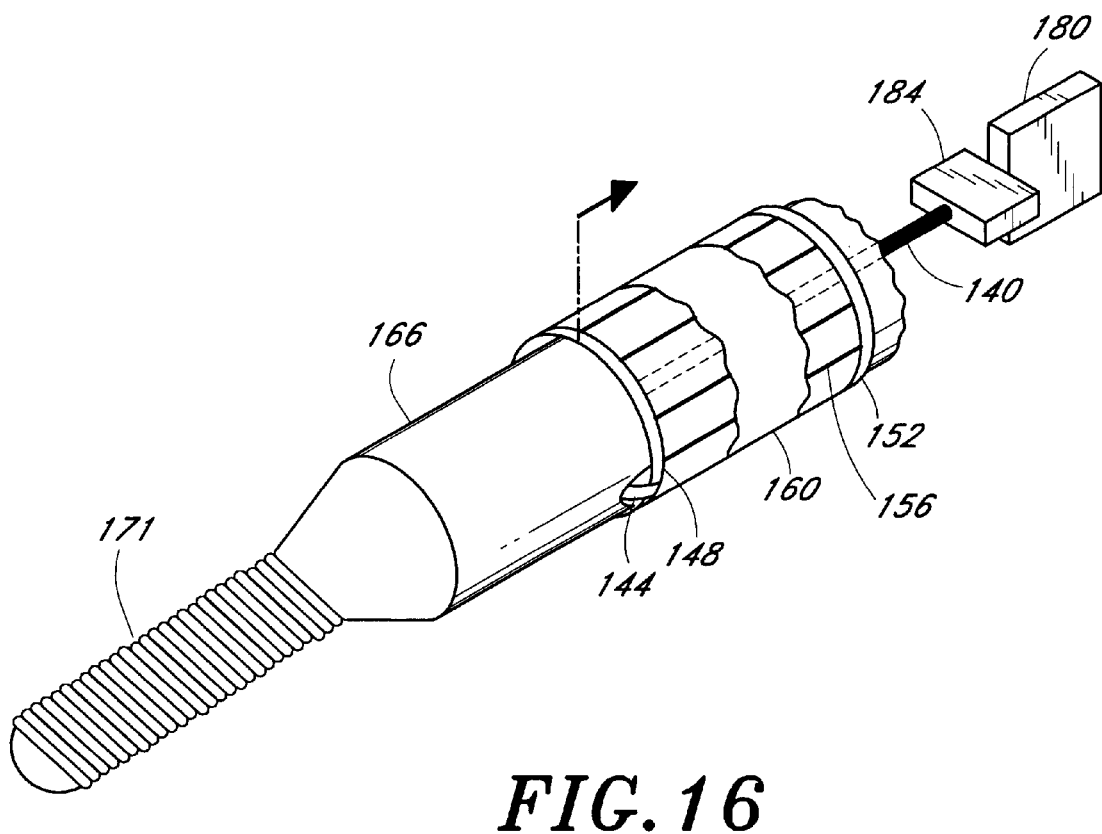
FIG. 16 is a side partial sectional view of the embodiment of FIG. 15 in which the ribbons are in their relaxed, undeployed position.
Figure 17:
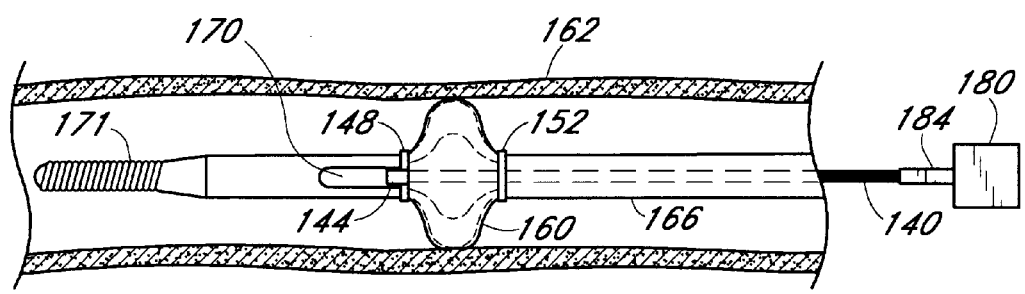
FIG. 17 is a side elevational view of the embodiment of FIG. 15 in which the ribbons are deployed, and the membrane makes a seal with the vessel.

Other non-self-expanding sealing mechanisms that can be used for occluding a vessel are described below. In the embodiment of FIGS. 15–17, a first elongate member 140, preferably a pull wire, is (when the device is completely assembled) attached to a brace member 144 that is in turn attached to a first ring member 148. Adjoining the first ring member 148 and a second ring member 152 are a plurality of ribbons 156 that extend between the two ring members. Surrounding the ribbons 156 is a membrane 160 that forms a seal with the patient's vessel 162 when the ribbons are expanded. The membrane 160 is joined to at least one and preferably both of the ring members 148 and 152. The membrane 160 can be joined to only one of the ring members 148 and 152, for example, when the membrane 160 extends far enough in the longitudinal direction to permit the membrane to make a good seal with the vessel 162 when the ribbons 156 are deployed.

To assemble the device, the first and second ring members 148 and 152, the ribbons 156, and the membrane 160 are placed as a unit around a second elongate member 166, which has a pair of oppositely facing holes 170 and 172. The brace member 144 is inserted through the holes 170 and 172 and secured to both the pull wire 140 and the first ring member 148. Further, the second ring member 152 is secured to the second elongate member 166. This assembled configuration, with the ribbons 156 in their longitudinal orientation, is illustrated in FIG. 16. As illustrated in FIG. 17, when the pull wire 140 is retracted, the ribbons 156 (shown in phantom) and the membrane 160 that surrounds them are urged towards the vessel 162, where the membrane makes a seal with the vessel. The ribbons 156 are preferably resilient enough so that they return to their longitudinal orientation when the pull wire 140 is released. The elasticity and resilience of the pull wire 140 also helps the ribbons 156 return to their undeployed configuration. A guidewire tip 171 may be used to assist in guiding the device to the desired location in the vessel 162.

Figure 18A:
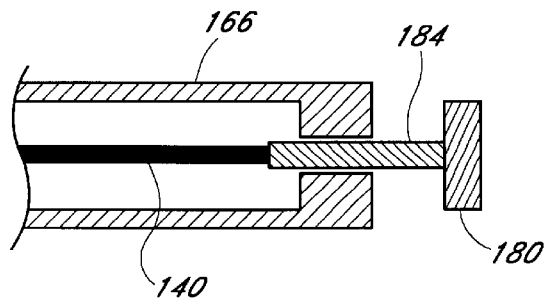
FIGS. 18A and 18B show longitudinal and end perspective views, respectively, of a locking mechanism used with a wire that deploys an expansion member.
Figure 18B:
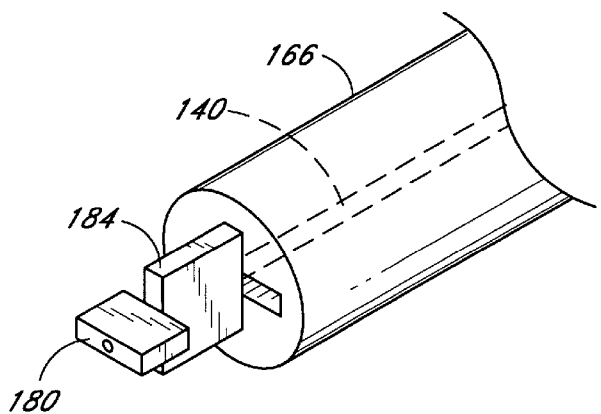

A preferred way of retracting the pull wire 140 is shown in FIGS. 18A and 18B. FIG. 18A shows the pull wire 140, which is attached to the brace member 144. A rotatable handle 180 is attached to a locking member 184 which in turn is fastened to the pull wire 140. When the locking member 184 clears the second elongate member 166 within which it resides (which is preferably outside the patient), the locking member and rotatable handle 180 may be oriented as illustrated in FIG. 18B to keep the pull wire 140 taught, thereby preventing the sealing mechanism from returning to its undeployed position. The pull wire 140 may be made of stainless or nitinol and may have a diameter of 0.006–0.008 inches, for a catheter having an O.D. of 0.014", for example.

Figure 19:
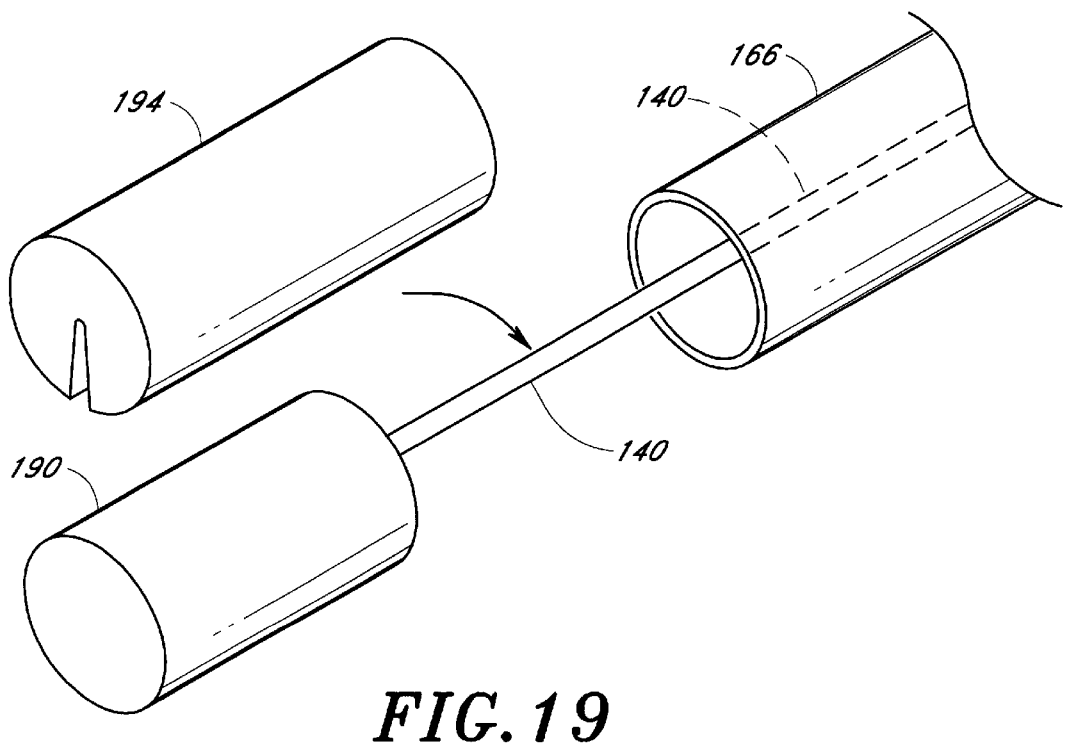
FIG. 19 is a perspective view of an alternative locking mechanism used with a wire that deploys an expansion member.

An alternative to the deployment apparatus illustrated in FIGS. 18A and 18B is shown in FIG. 19, in which a handle member 190 is grasped by the clinician to retract the pull wire 140, thereby deploying the sealing mechanism. Once extended, the sealing mechanism preferably has the tendency to return to its undeployed position, which in the process pulls the pull wire 140 back into the second elongate member 166. This can be prevented by inserting a spacer member 194 between the handle member 190 and the second elongate member 166. After the medical procedure is complete, and occlusion of the vessel is no longer required, the spacer member 194 can be removed and the pull wire 140 and the sealing mechanism returned to their respective undeployed positions. The device can then be removed from the patient.

Although the principle of using a non-self-expanding mechanism has been illustrated in FIGS. 15–17 with respect to deformable ribbons, other non-selfexpanding mechanisms, as illustrated in FIGS. 20A–20D, can be employed in conjunction with the brace member 144 and the first and second ring members 148 and 152. For example, instead of using ribbons 156, a non-self-expanding braided structure 200 can be used, in which the braided structure 200 adjoins first and second ring members 148 and 152 and is covered with a membrane 160 to form the unit 204 shown in FIG. 20A. The unit 204 can be used in conjunction with an elongate member 166, a brace member 144, a guidewire tip 171, a first elongate member 140 such as a pull wire, a rotatable handle 180, and a locking member 184 to form a device analogous to the ribbon-based device of FIG. 15. Alternatively, other mechanisms can be used for securing the pull wire 140, such as a handle member 190 and a spacer member 194.

Figure 20A:
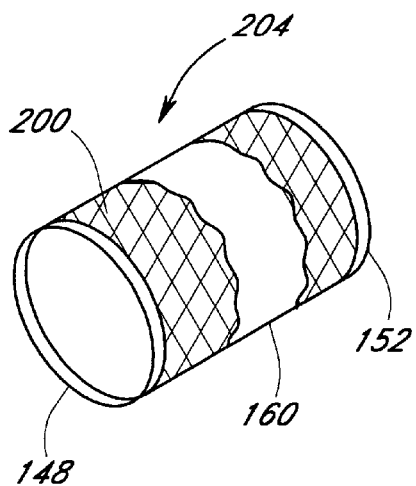
FIGS. 20A, 20B, 20C, and 20D show, respectively, a braid, a filter-like mesh, a slotted tube, and a plurality of coils, which can be used as alternative expansion members in place of the ribbons in the embodiment of FIG. 15.
Figure 20B:
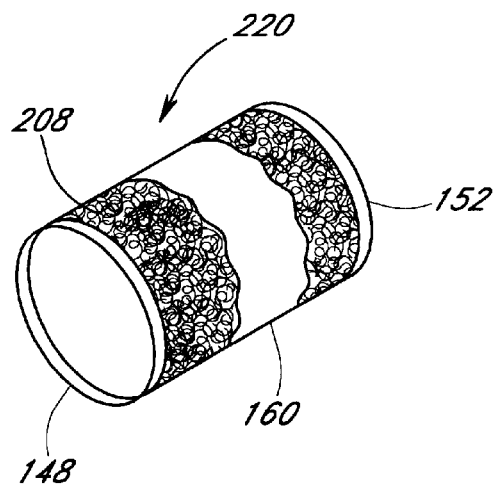
Figure 20C:
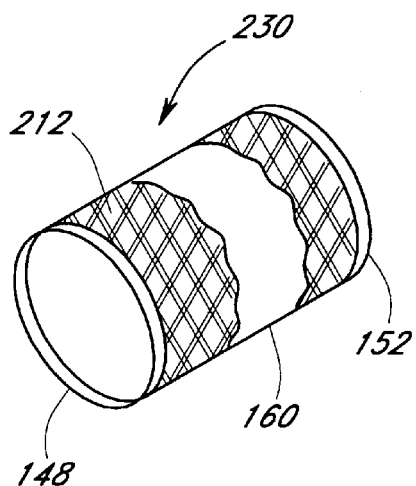
Figure 20D:
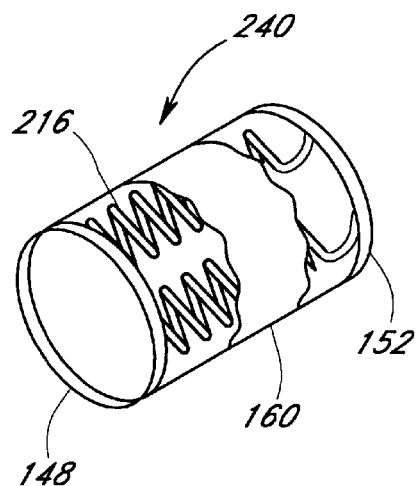

Other non-self-expanding mechanisms such as a filter-like mesh 208, a slotted tube 212, and coils 216 can be used to form units 220, 230, and 240 analogous to the braided structure unit 204 as shown in FIGS. 20B, 20C, and 20D. Units 220, 230, and 240 can likewise be used to construct devices analogous to the ribbon-based device illustrated in FIGS. 15–19. Further, if unit 204 is used without a membrane, it may assist in blood perfusion if the braided structure 200 is suitably constructed. Alternatively, perforated membranes like membranes 36' of FIG. 6B may be used to permit blood perfusion. Although the ribbons 156, the braided structure 200, the filter-like mesh 208, the slotted tube 212, and the coils 216 must be actively deployed (e.g. with a pull wire 140), they are nevertheless similar to their self-expanding counterparts.

It should be understood that the scope of the present invention is not be limited by the illustrations or the foregoing description thereof, but rather by the appended claims, and certain variations and modifications of this invention will suggest themselves to one of ordinary skill in the art.

What is claimed is:

1. A device for occluding a vascular segment, comprising:
   a tubular member having an expandable member at a distal end portion thereof, said tubular member configured for insertion into a blood vessel, said tubular member defining a lumen having at its proximal section a transverse surface at least partially occluding said lumen, said transverse surface having an opening of a first transverse profile;
   an elogated member within said tubular member and passing through said opening of said tubular member promixal section, said expandable member connected to a distal end portion of said elongate member, said elongate member expanding said expandable member into contact with the blood vessel as said tubular member and said elongate member are moved with respect to each other; and
   a lock fixed on a proximal portion of said elongate member which engages said transverse surface of said tubular member, without extending radially beyond an outer surface of said tubular member, to prevent movement of said elongate member in at least one direction with respect to said tubular member when said expandable member is expanded to contact the blood vessel;
   said lock having a second transverse profile which, when said expandable member is expanded, interferes with said first transverse profile of said opening of said tubular member proximal section.

2. The device of claim 1, further comprising a material that adjoins said expandable member for creating a seal with the vascular segment.

3. The device of claim 2, wherein said material does not completely encapsulate said expandable member.

4. The device of claim 1, wherein said expandable member comprises a member selected from the group consisting of a braid, a coil, a ribbon-like structure, a slotted tube, a plurality of ribs and a filter-like mesh.

5. The device of claim 1, wherein said expandable member expands as said elongate member is retracted.

6. The apparatus of claim 1, wherein said elongate member comprises a pull wire.

7. The apparatus of claim 1, wherein said lock comprises a handle and a locking member.

8. The apparatus of claim 1, wherein said expandable member occludes the blood vessel when said expandable member contacts the blood vessel.

9. The apparatus of claim 8, wherein said expandable member has holes therein to allow for the perfusion of blood when said expandable member is expanded.

10. The apparatus of claim 1, wherein said lock is located outside of the blood vessel.

11. The device claim 1, wherein said lock is proximal to said tubular member.

12. The device of claim 1, in which said expandable member has the tendency to return to an undeployed, relaxed state from a deployed, expanded state.

13. The device of claim 1, wherein said tubular member and said elongate member are moved longitudinally with respect to each other to expand said expandable member.

14. A method of occluding a segment with blood vessel, comprising:

inserting a tubular member into the blood vessel, the tubular member having an expandable member at a distal portion thereof;

inserting an elongate member within the blood vessel, the elongate member positioned within the tubular member and including a distal portion which is connected to the expandable member;

passing the elongate member through a transverse opening formed is a proximal section of the tubular member, the opening having a first profile;

expanding the expandable member into contact with the blood vessel by moving the tubular member and the elongate member with respect to each other;

moving a lock at a proximal portion of the elongate member into a locked configuration to prevent movement of the elongate member and the tubular member with respect to each other in at least one direction, the lock having a second profile which is different from but engages and interferes with the first profile of the opening of the tubular member, the lock not extending in the radial sense beyond an outer surface of the tubular member, so that the expandable member remains in contact with the blood vessel; and maintaining the lock in the locked configuration without the lock extending in the radial sense beyond an outer surface of the tubular member.

15. The method of claim 14, comprising retracting the elongate member to expand the expandable member.

16. The method of claim 15, in which said retracting the elongate member causes the expandable member to expand and form a seal with the blood vessel.

17. The method of claim 15, in which the longitudinal position of the elongate member is varied with respect to the longitudinal position of the tubular member to expand the expandable member until the vessel is occluded.

18. The method of claim 17, further comprising:

performing a medical procedure near the segment; and retrieving the elongate member, the tubular member and the expandable member from the vessel.

19. An apparatus, comprising:

a tubular member having an expandable member at a distal end portion thereof, said tubular member configured for insertion into a blood vessel, said tubular member defining a lumen and having at its proximal section an opening of a first transverse profile;

an elongate member within said tubular member passing through said opening of said tubular member proximal section and which is connected to said expandable member to expand said expandable member into contact with the blood vessel as said tubular member and said elongate member are moved with respect to each other; and a lock at a proximal portion of said elongate member which is adjustable between a locked configuration, and an unlocked configuration, wherein:

the locked configuration prevents movement of said elongate member and said tubular member with respect to each other through interference of a second transverse profile of said lock with the first transverse profile of said opening in said tubular member; and the unlocked configuration permits said lock to slide within said tubular member.

20. The device of claim 19, further comprising a material that adjoins said expandable member for creating a seal with the vascular segment.

21. The device of claim 20, wherein said material does not completely encapsulate said expandable member.

22. The device of claim 19, wherein said expandable member comprises a member selected from the group consisting of a braid, a coil, a ribbon-like structure, a slotted tube, a plurality of ribs and a filter-like mesh.

23. The device of claim 19, wherein said expandable member expands as said elongate member is retracted.

24. The apparatus of claim 19, wherein said elongate member comprises a pull wire.

25. The apparatus of claim 19, wherein said lock comprises a handle and a locking member.

26. The apparatus of claim 19, wherein said expandable member occludes the blood vessel when said expandable member contacts the blood vessel.

27. The apparatus of claim 26, wherein said expandable member has holes therein to allow for the perfusion of blood when said expandable member is expanded.

28. The apparatus of claim 19, wherein said lock is located outside of the blood vessel.

29. The apparatus of claim 19, wherein said lock is proximal to said tubular member.

30. The apparatus of claim 19, wherein said tubular member is insertable into the blood vessel when said expandable member is in an undeployed, relaxed state.

31. The apparatus of claim 19, wherein said expandable member is connected to a distal end portion of said elongate member.

32. The apparatus of claim 19, wherein said lock contacts said elongate member and said tubular member.

33. The apparatus of claim 19, wherein said tubular member and said elongate member are moved longitudinally with respect to each other to expand said expandable member.

* * * * *

UNITED STATES PATENT AND TRADEMARK OFFICE
CERTIFICATE OF CORRECTION

PATENT NO.   : 6,312,407 B1
DATED        : November 6, 2001
INVENTOR(S)  : Gholam-Reza Zadno-Azizi It is certified that error appears in the above-identified patent and that said Letters Patent is hereby corrected as shown below:

<u>Title page,</u>
Item [75], Inventors, Gholam-Reza Zadno-Azizi is the sole inventor, and any and all other names are hereby deleted.

Signed and Sealed this

Twenty-first Day of January, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,312,407 B1
DATED : November 6, 2001
INVENTOR(S) : Gholam-Reza Zadno-Azizi It is certified that error appears in the above-identified patent and that said Letters Patent is hereby corrected as shown below:

Column 10,
Line 36, "elogated" should be -- elongate --.
Line 37, "promixal" should be -- proximal --.

Signed and Sealed this

Eighth Day of April, 2003

JAMES E. ROGAN
*Director of the United States Patent and Trademark Office*